United States Patent
Alhuwaish et al.

(10) Patent No.: US 10,588,716 B1
(45) Date of Patent: Mar. 17, 2020

(54) PLIERS FOR MEASURABLE TORQUING IN ORTHODONTIC ARCHWIRES

(71) Applicant: KING SAUD UNIVERSITY, Riyadh (SA)

(72) Inventors: Hessah Abdullah M. Alhuwaish, Riyadh (SA); Abdullah Mohammad Aldrees, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/271,537

(22) Filed: Feb. 8, 2019

(51) Int. Cl.
*A61C 7/04* (2006.01)

(52) U.S. Cl.
CPC ..................... *A61C 7/04* (2013.01)

(58) Field of Classification Search
CPC .. A61C 7/04; A61C 7/026; A61C 7/02; B21F 3/00; B21F 1/06; B25B 7/00; B25B 7/02
See application file for complete search history.

(56) References Cited

U.S. PATENT DOCUMENTS

| | | | |
|---|---|---|---|
| 1,299,103 A * | 4/1919 | Angle | A61C 7/04 433/4 |
| 2,396,619 A * | 3/1946 | Strayer | A61C 7/04 433/4 |
| 3,727,316 A * | 4/1973 | Goldberg | A61C 7/04 433/4 |
| 4,043,364 A | 8/1977 | Rose | |
| 4,184,259 A | 1/1980 | Sosnay | |
| 4,979,312 A | 12/1990 | Wool | |
| 6,164,107 A | 12/2000 | Korba, Jr. | |
| 7,967,602 B2 | 6/2011 | Lindquist | |
| 8,052,420 B2 | 11/2011 | Navarro | |
| 9,774,003 B2 | 9/2017 | Naraoka | |
| 2009/0253093 A1 * | 10/2009 | Albaya | A61C 7/04 433/4 |

FOREIGN PATENT DOCUMENTS

CN          203837637 U          9/2014

* cited by examiner

*Primary Examiner* — Heidi M Eide
*Assistant Examiner* — Drew S Folgmann
(74) *Attorney, Agent, or Firm* — Richard C. Litman; Nath, Goldberg & Meyer

(57) ABSTRACT

Pliers for making measurable torque bends in orthodontic archwires include upper and lower grips that are pivotally connected to each other. The upper grip is attached to a lower jaw having a first lower wing and a second lower wing. At least one slot is defined in an upper surface of each lower wing for receiving a portion of an archwire therein. The lower grip is attached to an upper jaw. The upper jaw includes a first upper wing and a second upper wing. A pivoting rod is pivotally connected to the first and second upper wings. A lever arm slidably engages a central portion of the pivoting rod. End portions of the pivoting rod extend through the upper wings and are connected to protractors. The lever arm includes at least one channel on a bottom surface for receiving a portion of the archwire between the lower wings.

6 Claims, 5 Drawing Sheets

PLIERS FOR MEASURABLE TORQUING IN ORTHODONTIC ARCHWIRES

BACKGROUND

1. Field

The disclosure of the present patent application relates to orthodontic tools and particularly to pliers for making measurable torquing bends in orthodontic archwires.

2. Description of the Related Art

Fixed orthodontic appliances typically include a set of brackets bonded to the patient's teeth surfaces and archwires (thin bendable wires with a generally rectangular cross-section) made from different materials. Each bracket has a slot to receive the archwire. At certain stages in orthodontic treatment, it is necessary to bend the wire to deliver corrective forces to mal-positioned teeth.

Toward the end of orthodontic treatment (finishing stage), it is common to find a crown that is generally properly located and tooth root or roots angled labially or buccally (toward the lips or cheeks) or lingually (toward the tongue) out of the ideal position. To correct this problem, bends or twists on the orthodontic wires are necessary to provide the necessary corrective force. The force expressed via the twist or bend belt on the archwire is called the torquing force because this force tends to rotate the tooth around its center of resistance.

Typically, creating a bend belt requires two tools, one that holds the wire at two points and a second that is used to twist the wire. This technique is cumbersome and lacks accuracy because it is difficult to measure the bend magnitude.

Accordingly, pliers for making measurable torque bends in orthodontic archwires is desirable.

SUMMARY

Pliers for making measurable torque bends in orthodontic archwires include a handle having an upper grip and a lower grip. The upper and lower grips are pivotally connected to each other. A lower jaw includes a first lower wing and a second lower wing spaced from the first lower wing. At least one slot is defined in an upper surface of each lower wing for receiving a portion of an archwire therein. The upper jaw includes a first upper wing and a second upper wing spaced from the first upper wing. A pivoting rod extends between and is pivotally connected to the first and second upper wings. A lever arm slidably engages the pivoting rod. The lever arm has a vertical slot for receiving a central portion of the pivoting rod therein. End portions of the pivoting rod extend out of the lever arm through the upper wings. Each of the end portions are connected to a respective protractor. The lever arm includes at least one channel on a bottom surface.

The upper and lower jaws can be separated to position an archwire in the slots of the lower wings. The jaws can then be closed on the archwire and the lever arm can be lowered such that the channel receives at least a portion of the archwire extending between the lower wings. The lever arm can then be rotated to axially rotate the portion of the archwire in the channel. The magnitude of the bend can be determined by indicia on the protractors.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
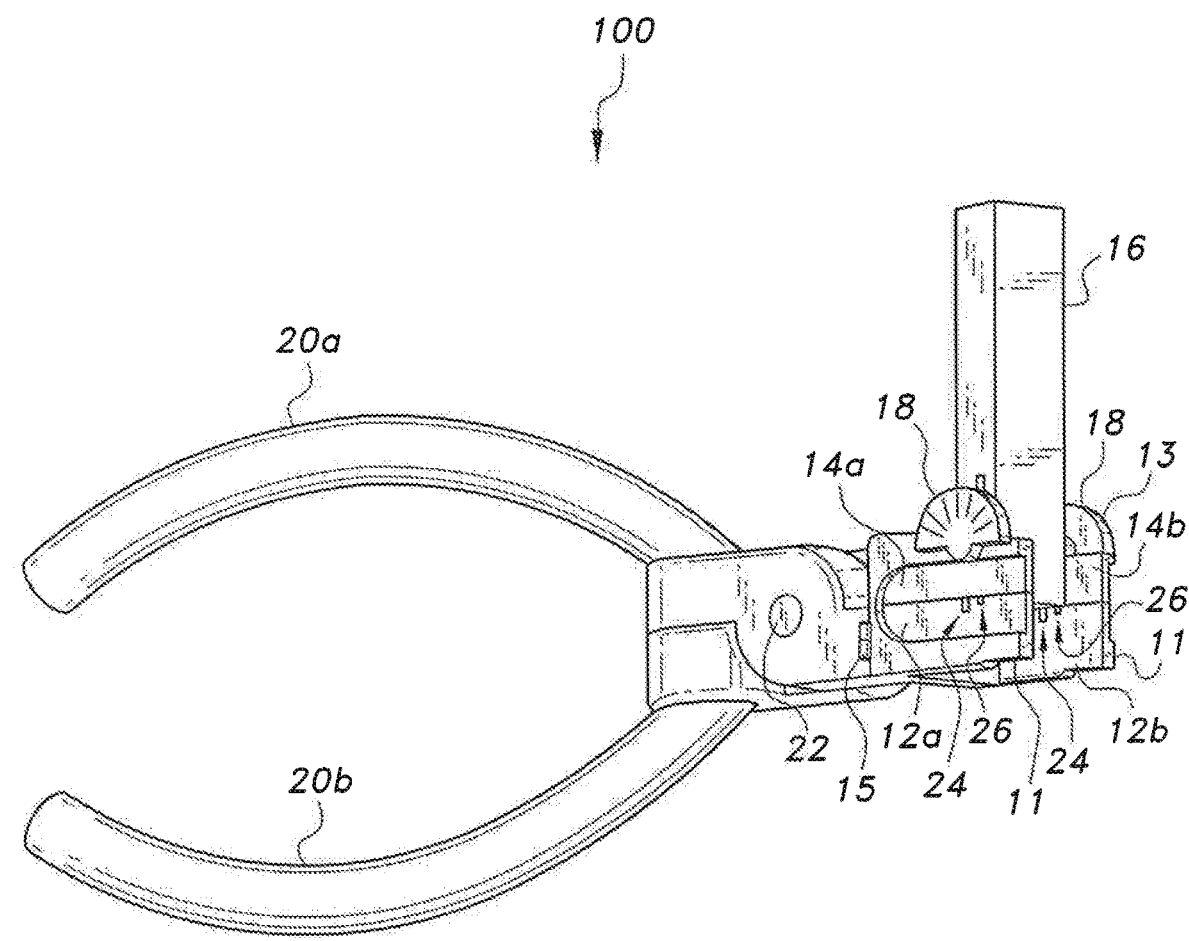
FIG. 1 is a perspective view of pliers for making measurable torquing bends in an archwire.
Figure 3:
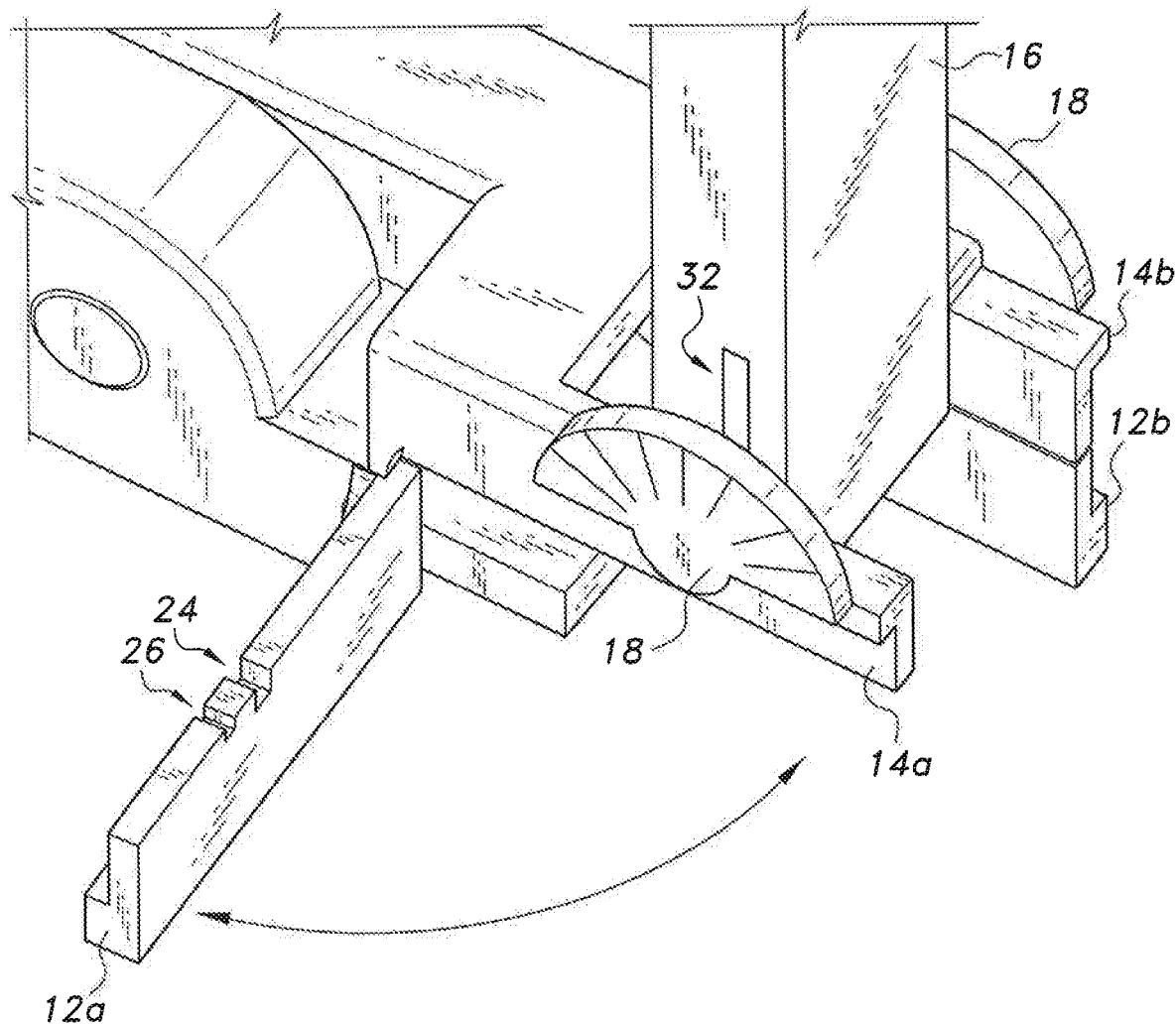
FIG. 3 is an enlarged view of the jaws of the pliers shown in FIG. 1, with one of the lower wings pivoted open.

FIG. 1 shows an embodiment of pliers 100 for making measurable torque bends in orthodontic archwires. The pliers 100 include a handle having an upper grip 20a and a lower grip 20b. The grips 20a, 20b are pivotally connected to each other by a hinge pin 22. The upper grip 20a is attached to a lower jaw 11 which includes a first lower wing 12a and a second lower wing 12b. Lower wing 12a can be connected to the upper grip 20a by a hinge 15. As such, the lower wing 12a can be pivoted in a direction away from the lower wing 12b when desired, as shown in FIG. 3 and described in detail herein. Two slots 24, 26, e.g., rectangular slots, are defined in an upper surface of each lower wing 12a, 12b for receiving a portion of an archwire therein. The two slots 24, 26 can be configured for receiving different archwires. As such, slot 24 can have a different size and/or shape than slot 26, When the archwire is properly positioned in slot 24 or slot 26 of the lower jaw 11, a first portion of the archwire is held by the first lower wing and a second portion of the archwire is held by the second lower wing.

The lower grip 20b is attached to an upper jaw 13 which includes a first upper wing 14a and a second upper wing 14b. The upper wings 14a, 14b can be configured to be identical to the lower wings 12a, 12b except that the upper wings 14a, 14b can be devoid of slots 24, 26 and hinge 15. A pivoting rod 34 (FIGS. 5A-5B) extends between and is pivotally connected to the upper wings 14a and 14h. A lever arm 16 slidably engages the pivoting rod 34. The lever arm 16 has a vertical slot 32 for receiving a central portion of the pivoting rod 34 therein. The central portion of the pivoting rod 34 is slidably retained within the lever arm 16 and first and second end portions of the pivoting rod 34 extend out of the lever arm 16 through upper wings 14a, 14b, respectively. A first protractor 18 is fixedly connected to the first end of the pivoting rod 34 and a second protractor is fixedly connected to the second end of the pivoting rod 34. As with conventional protractors, protractors 18 can include indicia for angle measurement. The lever arm 16 includes channels 28, 30 defined within a bottom surface thereof. The channels 28, 30 can be aligned with slots 24, 26, respectively, of the lower wings 12a, 12b when the lever arm 16 is lowered. Thus, when the lever arm 16 is lowered, a portion of the archwire extending between the lower wings 12a, 12b can be received within channel 28 or channel 30.

Figure 5A:
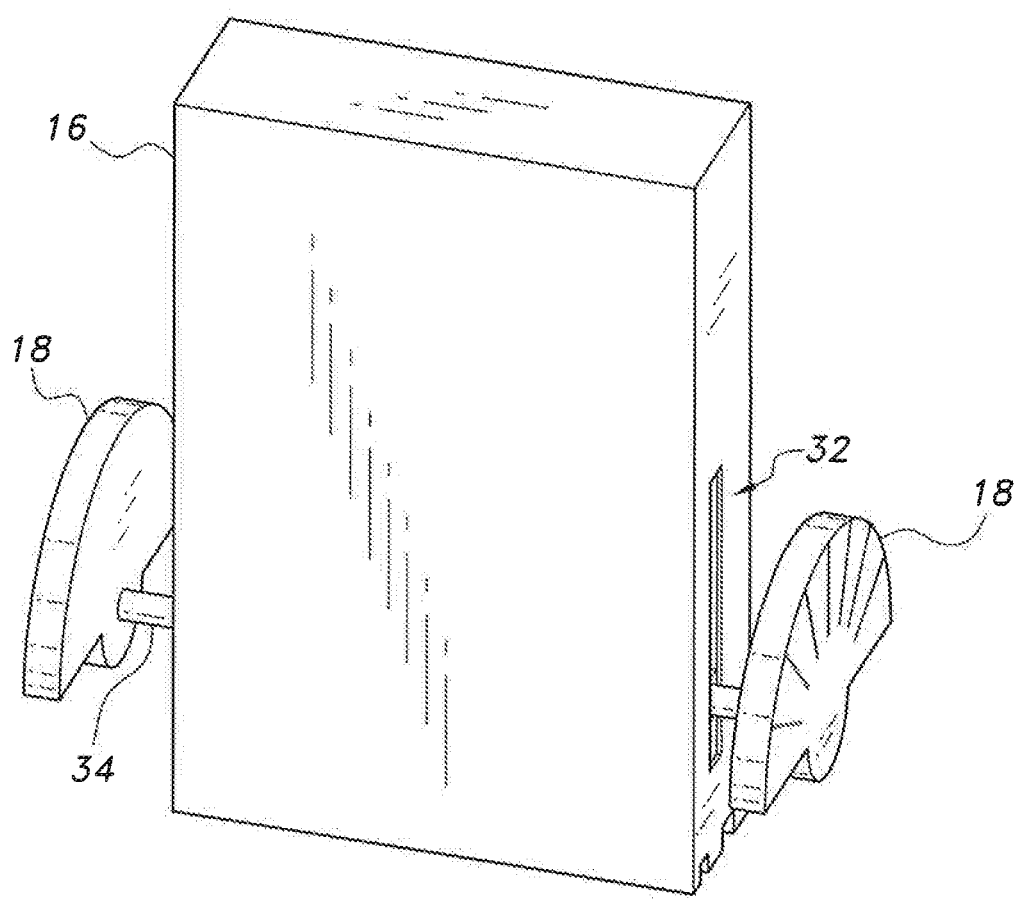
FIG. 5A is an enlarged perspective view of the lever arm and attached protractors.
Figure 5B:
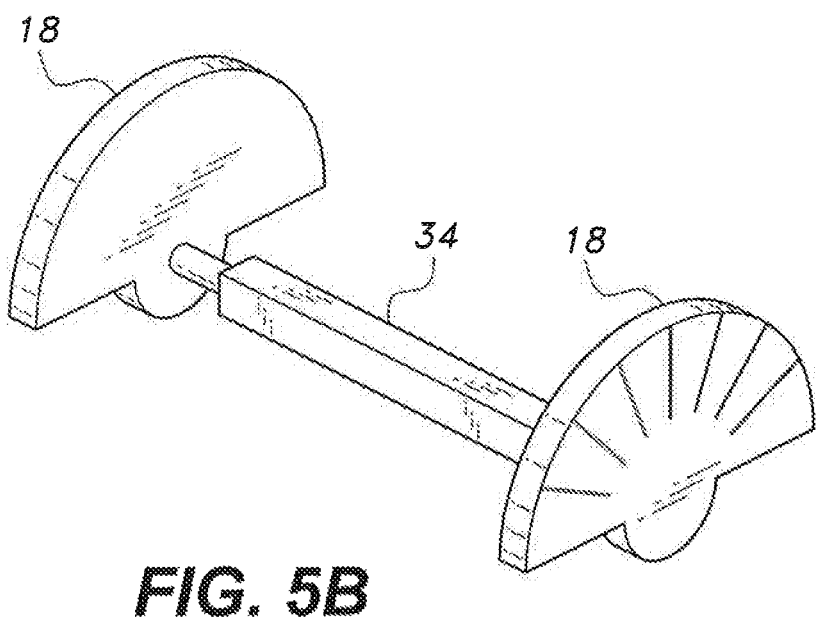
FIG. 5B is an enlarged perspective view of the pivoting rod and attached protractors.

As shown in FIG. 5A, the protractors 18 are rigidly attached to opposing ends of the pivoting rod 34 which extend through the upper wings 14a, 14b. As shown in FIG. 5B, the central portion of the pivoting rod 34 can have a rectangular or square cross-section and end portions of the pivoting rod 34 can have a circular cross-section. The circular end portions of the pivoting rod 34 extend through the upper wings 14a, 14b and act as a hinge pin for pivoting the lever arm 16. As such, the lever arm 16, pivoting rod 34, and protractors 18 experience the same rotational movement when the lever arm 16 is rotated.

The central portion of the pivoting rod 34 is sized to fit snugly within the slot of the lever arm, while allowing vertical movement of the lever arm. For example, two opposing side walls of the pivoting rod 34 slidably contact inner walls of the lever arm 16 within the slot 32 (FIG. 5A) to allow the lever arm 16 to be selectively lifted and lowered. The lever arm 16 can be lifted while the archwire is being positioned between the jaws 11, 13 and lowered on the archwire after the jaws 11, 13 are shut. In addition, once the archwire is bent, the lever arm 16 can be lifted off the archwire so that jaws 11, 13 can be opened without disrupting the precise bend applied using the lever arm 16.

In use, the grips 20a, 20b can be pivoted away from each other to separate the lower wings 12a, 12b from the upper wings 14a, 14b. The grips 20a, 20b can be pivoted toward each other to cause upper surfaces of the lower wings 12a, 12b to contact the lower surfaces of the upper wings 14a, 14h and shut the jaws 11, 13. An archwire can be positioned in a slot 4 or slot 26 in the lower wings 12a, 12b (depending on the size of the archwire), and the jaws 11, 13 can be shut to lock the archwire in place. The lever arm 16 can be lowered over the archwire and positioned to receive the archwire in the channel 28 or 30 that is in alignment with the selected slot of the lower wings 12a, 12b. The lever arm can then be rotated to axially rotate the portion of the archwire in the channel 28 or 30. As a result, a bend belt having a length equal to the span between the wings 12a, 12b can be created in the archwire. The bend belt is axially offset from other portions of the wire. The magnitude of the bend can be determined by the indicia on the protractors 18.

Figure 2:
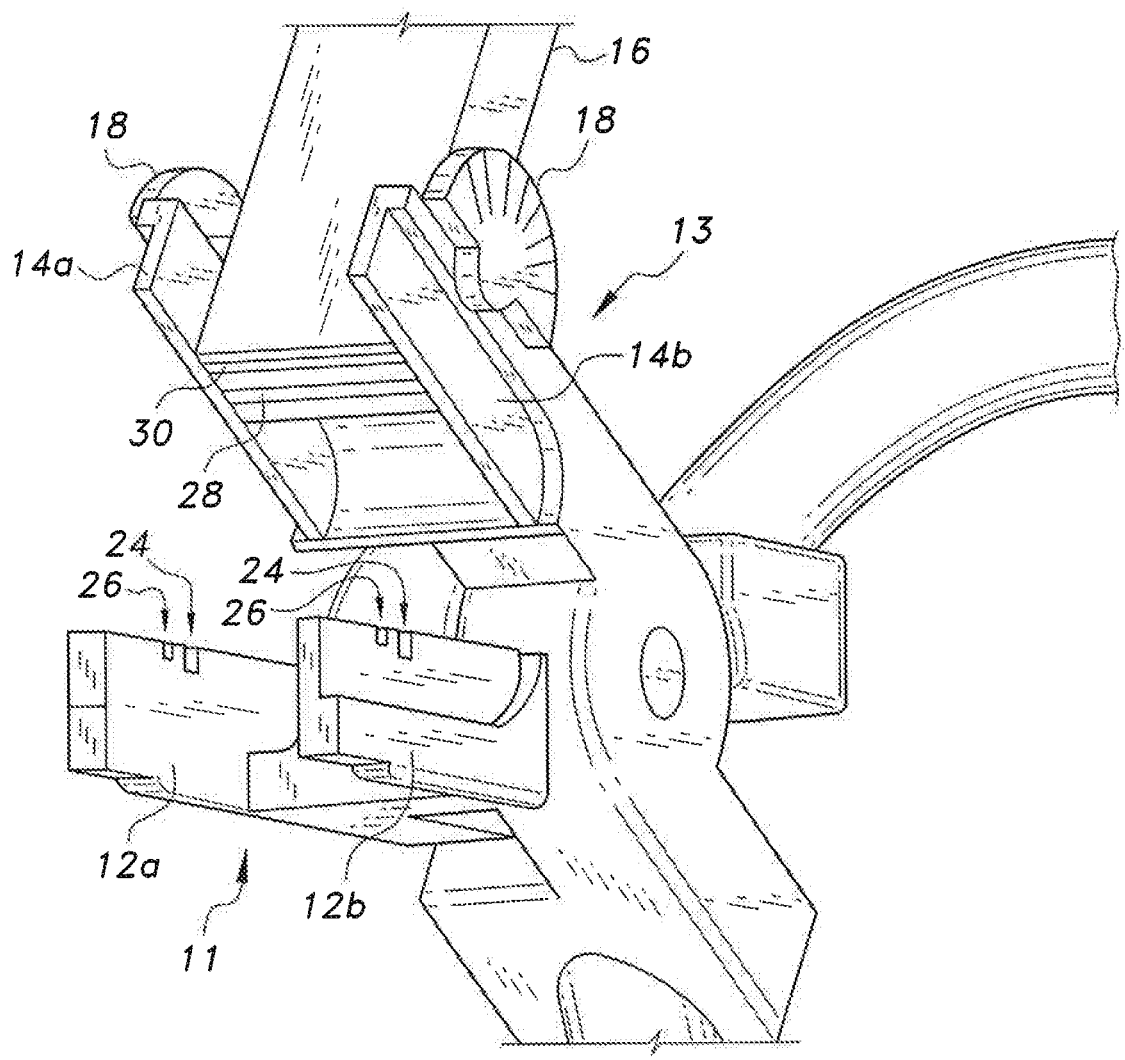
FIG. 2 is an enlarged perspective view of the jaws of the pliers shown in FIG. 1.

FIG. 2 shows the jaws 11, 13 of the pliers 100 in an open position. As shown in FIG. 2, channel 28 is larger than channel 30. Channels 28 and 30 are sized and positioned to align with the slots 24, 26, respectively, in the lower wings 12a, 12b. The slot 24 is aligned with channel 28. The slot 25 is aligned with channel 30. As such, when the jaws 11, 13 are closed, a continuous channel for receiving the archwire is formed. The slots 24, 26 and channels 28, 30 are rectangular in the figures for torquing rectangular wires. Other configurations of slots and channels for receiving wires of other cross-sections are contemplated. In some embodiments, there may be more or less than two slots.

When the lower right wing 12a is in a closed position, as seen in FIGS. 1-2, the pliers 100 will impart two bends in the archwire, with each bend point being adjacent a respective slot. In some embodiments, the distance between the wings 12a, 12b may be sized for creating a bend belt having a length that will span only a single tooth. However, in some cases, multiple adjacent teeth may require a similar torquing bend in the archwire. In these cases, it will be necessary to create a bend belt that is larger than the span between the jaw wings 12a. 12b. To achieve this, the lower right wing 12a may be pivoted open, as seen in FIG. 3, so the archwire is only held by slot 24 or 26 of the lower left wing 12b. By holding the archwire in only one of the lower wings, the lever arm 16 will impart only a single bend in the archwire. This allows the practitioner to create a bend belt having any desired length by creating one bend at a time along the length of the archwire.

Figure 4:
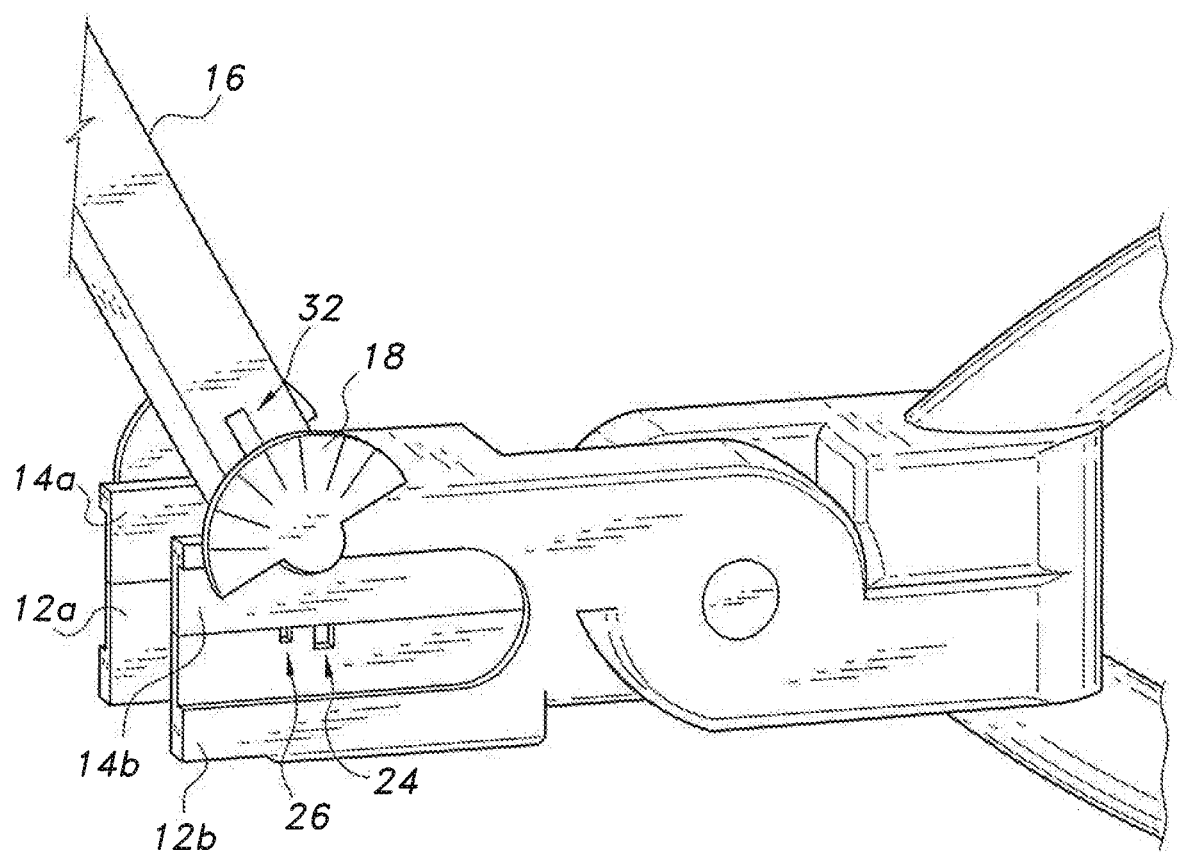
FIG. 4 is an enlarged, side view of the pliers of FIG. 1 showing the lever arm rotated in a wire bending position.

FIG. 4 shows the lever arm 15 at an angle that will apply an axial bend to an archwire running through the slots 24 or 26 of the lower wings. As seen in FIG. 4 the lever arm 16 has been rotated forward to apply a counter clockwise bend to an archwire, relative to the point of view of FIG. 4, The protractors are positioned to show the angle of the lever arm 16 with respect to a top edge of the upper wings. Thus, a practitioner can determine the exact angle of the bend using the protractors 18 attached to the lever arm 16. For example, if each line of the protractor in FIG. 4 indicates approximately 25 degrees, the archwire will be bent about 25.7 degrees when the lever arm 16 is in the position shown. In some embodiments, the protractors 18 may have more or less scale lines, or the protractors 18 may also include numbers that indicate degree offset from normal.

It is to be understood that the pliers for measurable torquing in an archwire is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. Pliers for making measurable torque bends in orthodontic archwires, comprising:

an upper grip and a lower grip pivotally connected to the upper grip;

a lower jaw extending from the upper grip, the lower jaw having a first lower wing and a second lower wing spaced from the first lower wing, wherein each lower wing includes an upper surface having first and second slots extending therethrough, wherein the first and second slots of the first lower wing are aligned with the first and second slots of the second lower wing so as to receive an archwire therein, further wherein the first slots on each of the first and second lower wings have a first configuration and the second slots on each of the first and second lower wings have a second configuration, the first and second configurations being dissimilar, wherein at least one of the first and second lower wings being pivotally attached to the lower jaw so as to pivotal away from the other lower wing thereby permitting the archwire to be held by the other lower wing alone;

an upper jaw extending from the lower grip over the lower jaw, the upper jaw having a first upper wing and a second upper wing spaced from the first upper wing;

a pivoting rod pivotally connected to the first and second upper wings, a central portion of the pivoting rod extending between the first and second upper wings and first and second end portions of the pivoting rod extending through the first and second upper wings, respectively;

a lever arm slidably engaging the central portion of the pivoting rod, the lever arm having a vertical slot extending therethrough and a pair of channels defined on a bottom surface of the lever arm, the vertical slot being spaced from the bottom surface, wherein the pair of channels being aligned with the first and second slots on the first and second lower wings when the lever arm is lowered so that a portion of the archwire extending between the first and second lower wings can be received within a respective channel, further wherein each of the pair of channels corresponds in configuration to its respective aligned slot;

a pair of protractors, each protractor connected to a respective end of the pivoting rod, wherein the pair of protractors are configured to slidably contact inner walls of the vertical slot as the lever arm is moved thereby indicating the angle of bend for the archwire.

2. The pliers according to claim 1, wherein the vertical slot of the lever arm and the central portion of the pivoting rod have a rectangular cross section.

3. The pliers according to claim 2, wherein opposing end portions of the pivoting rod have a circular cross section.

4. The pliers according to claim 1, wherein the protractor includes evenly dispersed, radially extending indicia.

5. The pliers according to claim 1, wherein the protractor has a semicircular shape with a curved upper edge and a straight lower edge, the straight edge of the protractor being aligned with a top edge of the upper wings when the lever arm is in an upright, vertical position.

6. The pliers according to claim 1, wherein the slots in the lower wings and the channel in the lever have a rectangular shape.

\* \* \* \* \*